(12) United States Patent
Katsuno et al.

(10) Patent No.: US 8,414,515 B2
(45) Date of Patent: Apr. 9, 2013

(54) BLOOD RESERVOIR

(75) Inventors: Yutaka Katsuno, Hiroshima (JP);
Minoru Tanaka, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 12/675,053

(22) PCT Filed: Aug. 21, 2008

(86) PCT No.: PCT/JP2008/064924
§ 371 (c)(1),
(2), (4) Date: Feb. 24, 2010

(87) PCT Pub. No.: WO2009/028397
PCT Pub. Date: Mar. 5, 2009

(65) Prior Publication Data
US 2011/0118648 A1    May 19, 2011

(30) Foreign Application Priority Data

Aug. 27, 2007 (JP) .................................. 2007-220213

(51) Int. Cl.
*A61M 37/00* (2006.01)
*A61M 1/00* (2006.01)
*B01D 21/24* (2006.01)

(52) U.S. Cl.
USPC .......................... 604/6.15; 422/44; 210/433.1

(58) Field of Classification Search ............ 604/19, 604/403, 411, 257, 258, 4.01–6.16; 138/111, 138/115; 422/44–48; 210/433.1, 436–437
See application file for complete search history.

(56) References Cited

U.S. PATENT DOCUMENTS

| 4,664,682 A * | 5/1987 | Monzen ........................... 96/179 |
| 4,705,497 A | 11/1987 | Shitaokoshi et al. |
| 4,976,708 A * | 12/1990 | Oshiyama ..................... 604/408 |
| 5,149,318 A * | 9/1992 | Lindsay ........................ 604/6.15 |
| 5,580,349 A * | 12/1996 | Thor et al. .................... 604/406 |
| 5,770,073 A * | 6/1998 | Bach et al. .................... 210/472 |
| 2002/0094300 A1 * | 7/2002 | Yokoyama et al. ............. 422/44 |

FOREIGN PATENT DOCUMENTS

| JP | 1-26704 | 5/1989 |
| JP | 2-124170 | 5/1990 |
| JP | 6-102088 | 12/1994 |
| JP | 2002-165878 | 6/2002 |

* cited by examiner

*Primary Examiner* — Philip R Wiest
(74) *Attorney, Agent, or Firm* — Hamre, Schumann, Mueller & Larson, P.C.

(57) ABSTRACT

A conduit tube (90) that communicates with an intracardiac blood inflow port (50) and a liquid medicine injection port (72) and allows blood from the intracardiac blood inflow port and a liquid medicine from the liquid medicine injection port to flow into a cardiotomy section (2) is inserted from above downward in the cardiotomy section 2. A blood flow channel (93) for the flow of blood and a liquid medicine flow channel (95) for the flow of a liquid medicine are formed independently of each other in the conduit tube. With respect to the vertical direction, the lower end of a blood conduit tube portion (94) that forms the blood flow channel is located at a lower position than the lower end of a liquid medicine conduit tube portion (96) that forms the liquid medicine flow channel. This prevents the generation of negative pressure in the liquid medicine flow channel due to the flow of blood. It also reduces the resistance to the inflow of a liquid medicine into the cardiotomy section.

7 Claims, 11 Drawing Sheets

BLOOD RESERVOIR

TECHNICAL FIELD

The present invention relates to a blood reservoir that temporarily stores extracorporeally circulating blood in an extracorporeal circulation circuit for use in cardiopulmonary surgeries or the like. In particular, it relates to a blood reservoir equipped with a built-in cardiotomy section that filters intracardiac blood.

BACKGROUND ART

For cardiac surgeries or the like, an extracorporeal circulation circuit equipped with a blood pump or an artificial lung serving as a substitute for the function of a patient's heart or lung is used. Such an extracorporeal circulation circuit is provided with a blood reservoir (sometimes referred to as a "venous blood reservoir") for temporarily storing venous blood removed from a patient's vein and adjusting the blood volume in a circulating circuit, and a blood reservoir (sometimes referred to as an "cardiotomy reservoir") for aspirating, collecting, and temporarily storing blood (intracardiac blood) flowing out of the operative field. As compared to the venous blood, the intracardiac blood contains a high proportion of air bubbles or extraneous materials, such as pieces of flesh, fats, and clots, so the cardiotomy reservoir is provided with a cardiotomy section composed of a filter for removing extraneous materials and a defoamer for defoaming. Storing both of the venous blood and the intracardiac blood in a common blood reservoir is also widely practiced.

FIG. 13 is a cross-sectional view illustrating an example of a general configuration of a conventional cardiotomy section 900. The cardiotomy section 900 includes a filter 910 having a generally cylindrical shape as a whole and a defoamer 920 having a generally cylindrical shape and located inside the filter 910. Generally disk-shaped resin plates 931 and 932 are bonded to the upper and lower edges of the filter 910. The defoamer 920 is held by being bonded to the upper resin plate 931. The upper resin plate 931 has a through hole 933 formed in the center thereof. A conduit tube 935 that introduces intracardiac blood into the cardiotomy section 900 is inserted in the through hole 933 (see Patent Document 1, for example).

A mixing vessel 940 is connected to the upstream side of the conduit tube 935. A space in the mixing vessel 940 is divided by a partition wall 943 into a blood flow channel 941 for the flow of blood and a liquid medicine flow channel 942 for the flow of a liquid medicine. The conduit tube 935 is connected to an opening 944 formed in the underside of the mixing vessel 940. The partition wall 943 roughly divides the opening 944 into two sections.

Blood (intracardiac blood) 951 aspirated from an operative field flows through an intracardiac blood inflow port 950, the blood flow channel 941 and the opening 944 in the mixing vessel 940, and the conduit tube 935 in sequence, and then into the cardiotomy section 900.

In the case of adding a liquid medicine to the blood in the cardiotomy section 900, a liquid medicine 961 is injected into a liquid medicine injection port 960 and flows through the liquid medicine flow channel 942 and the opening 944 in the mixing vessel 940 and the conduit tube 935 in sequence, and then into the cardiotomy section 900.

Patent Document 1: JP2002-165878A

DISCLOSURE OF INVENTION

Problem to be Solved by the Invention

In general, the flow rate of the blood 951 is higher than the flow rate of the liquid medicine 961, so that the conduit tube 935 forms what is called an aspirator depending on the flow of the blood 951 in the vicinity of the opening 944, and negative pressure builds up in the liquid medicine flow channel 942 accordingly. If negative pressure builds up in the liquid medicine flow channel 942, problems arise, such as the difficulty in controlling the flow rate of the liquid medicine 961.

In addition, it is desirable that the resistance to the inflow of the liquid medicine 961 into the cardiotomy section 900 should be low.

It is thus an object of the present invention to solve the above-described conventional problems and to provide a blood reservoir that is equipped with a conduit tube allowing blood and a liquid medicine to flow into a cardiotomy section and that is configured to suppress the generation of negative pressure in a liquid medicine flow channel due to the flow of blood and to reduce the resistance to the inflow of a liquid medicine into the cardiotomy section.

Means for Solving Problem

A blood reservoir according to the present invention includes a housing that includes an intracardiac blood inflow port and a liquid medicine injection port in an upper portion thereof and a blood outflow port at a lower end thereof, a cardiotomy section arranged in the housing; and a conduit tube that communicates with the intracardiac blood inflow port and the liquid medicine injection port and allows blood from the intracardiac blood inflow port and a liquid medicine from the liquid medicine injection port to flow into the cardiotomy section. The conduit tube is inserted from above downward in the cardiotomy section.

A blood flow channel for flow of blood and a liquid medicine flow channel for flow of a liquid medicine are formed independently of each other in the conduit tube.

With respect to a vertical direction, a lower end of a blood conduit tube portion that forms the blood flow channel is located at a lower position than a lower end of a liquid medicine conduit tube portion that forms the liquid medicine flow channel.

Effects of the Invention

In the blood reservoir according to the present invention, since the blood flow channel for the flow of blood and the liquid medicine flow channel for the flow of a liquid medicine are formed independently of each other in the conduit tube, the aspirator effect caused by the flow of blood will not occur, and accordingly negative pressure will not build up in the liquid medicine flow channel.

In addition, since the lower end of the blood conduit tube portion is located at a lower position than the lower end of the liquid medicine conduit tube portion with respect to the vertical direction, the resistance to the inflow of a liquid medicine into the cardiotomy section can be reduced.

DESCRIPTION OF THE INVENTION

Embodiment 1

Figure 1:
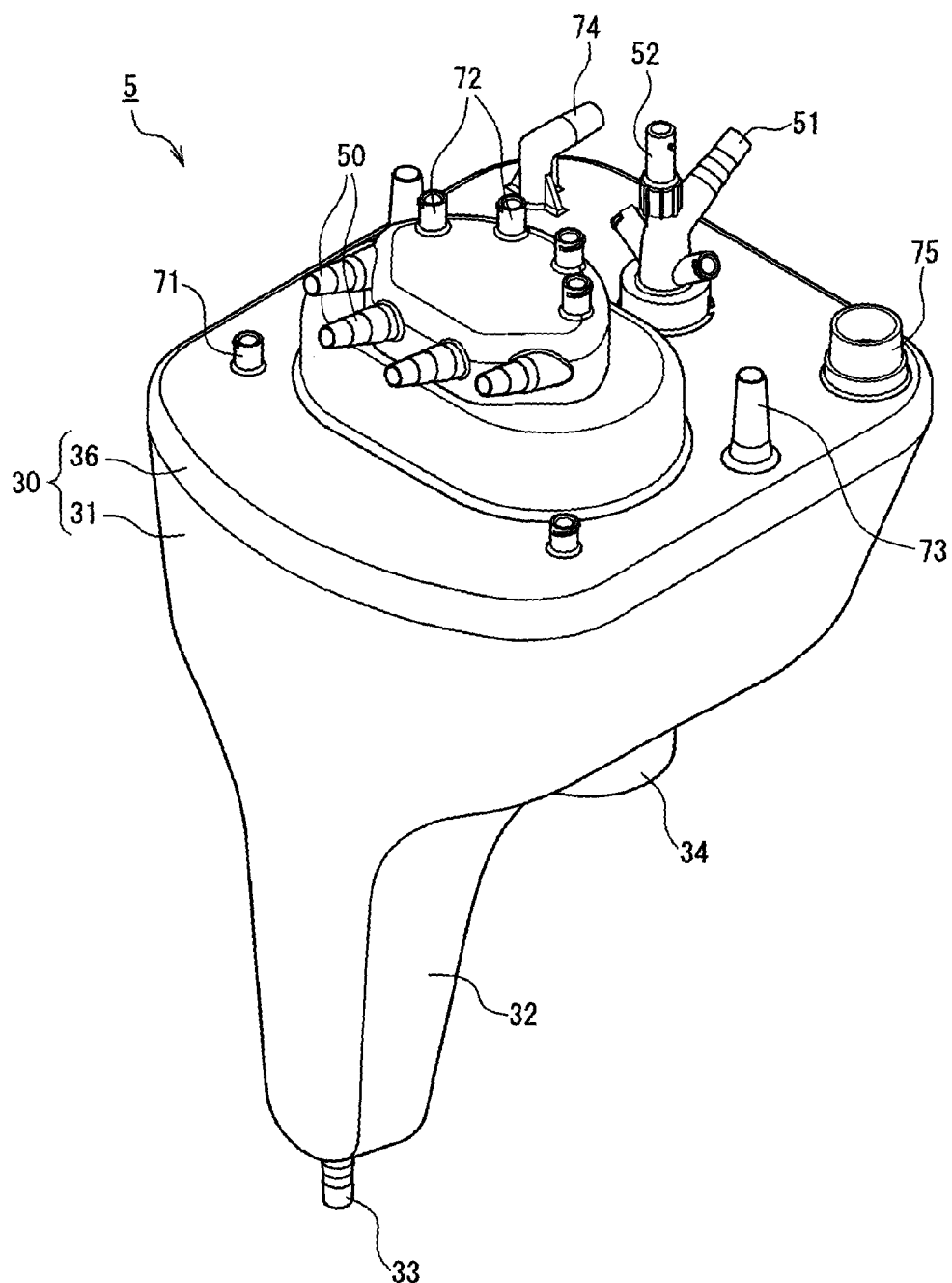
FIG. 1 is a perspective view illustrating a general configuration of a blood reservoir according to Embodiment 1 of the present invention.
Figure 2:
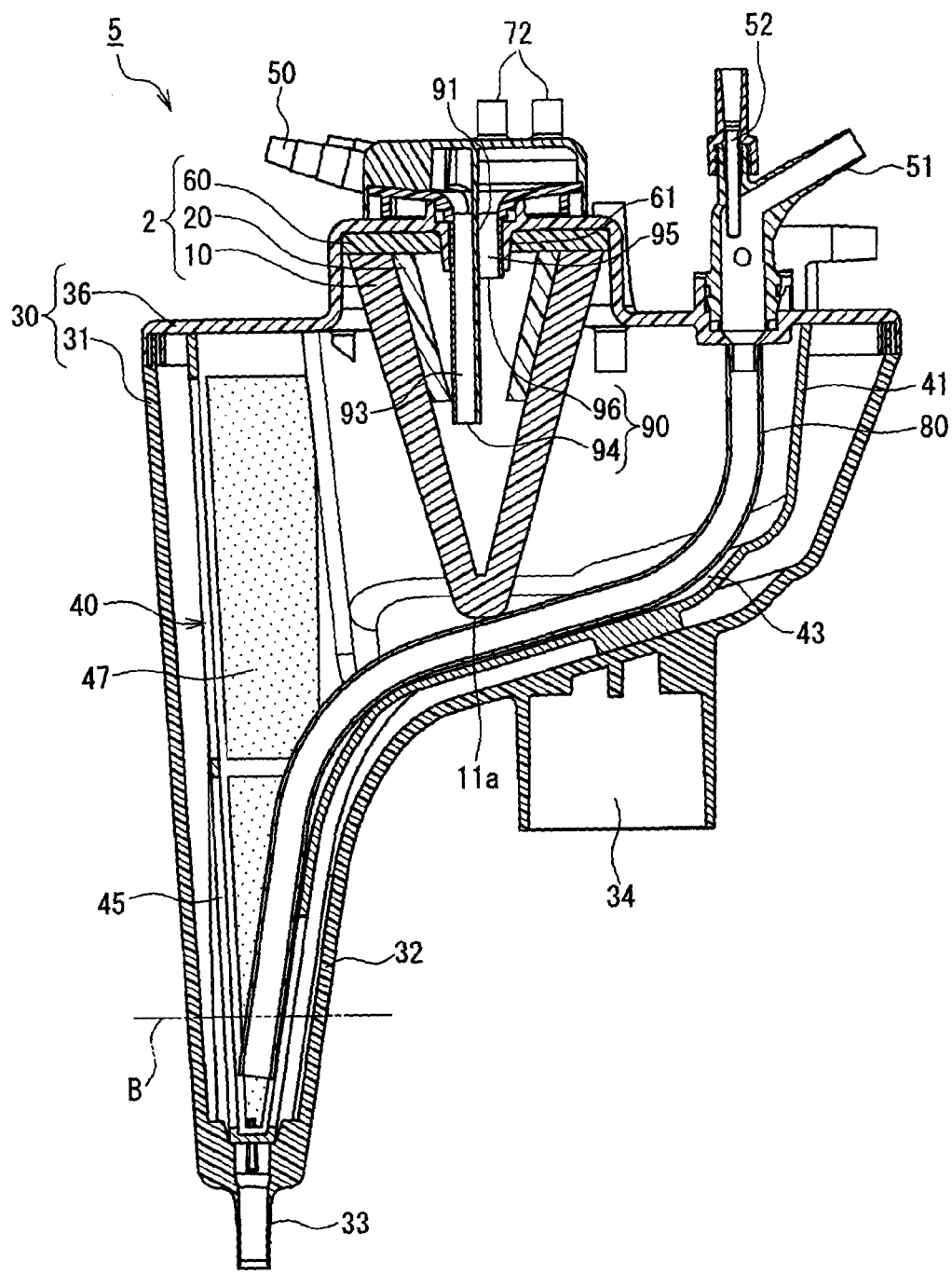
FIG. 2 is a cross-sectional side view illustrating a general configuration of the blood reservoir according to Embodiment 1 of the present invention.

FIG. 1 is a perspective view illustrating a general configuration of a blood reservoir 5 according to Embodiment 1 of the present invention, and FIG. 2 is a cross-sectional side view thereof. The blood reservoir 5 includes a housing 30 that is composed of a housing body 31 and a lid 36 placed on the top of the housing body 31.

The housing body 31 includes a blood storage section 32 that is formed by a non-central part of the bottom protruding downward, and a blood outflow port 33 that is provided at the lower end of the blood storage section 32 and allows the outflow of blood. A fixing hole 34 is formed in the underside of the housing body 31 in order to hold the blood reservoir 5 by inserting therein an upper end of a support provided upright in an operating room.

The lid 36 has mounted thereon multiple intracardiac blood inflow ports 50 that allow the inflow of intracardiac blood, and a venous blood inflow port 51 that allows the inflow of venous blood. The lid 36 further is provided with multiple liquid medicine injection ports 71 and 72 for mixing a liquid medicine or the like in blood, a service port 73 for mixing a large volume of liquid medicine into blood in an urgent need or for allowing the inflow of blood that has passed through an alternate cardiotomy section in a case where the filter 10 of the cardiotomy section 2 cannot be used because of clogging, an evacuation port 74 for adjusting pressure in the blood reservoir 5, a pressure regulating valve 75 for preventing development of an abnormal positive or negative pressure in the blood reservoir 5, and so on. The venous blood inflow port 51 has a temperature probe 52 stuck therein for measuring the temperature of venous blood.

The venous blood inflow port 51 is connected to a blood removal line tube in an extracorporeal circulation circuit, and the intracardiac blood inflow ports 50 are connected to intracardiac blood aspiration line tubes. The blood outflow port 33 is connected to a blood sending line tube in the extracorporeal circulation circuit. The liquid medicine injection ports 71 and 72 are connected to liquid medicine injection line tubes connected to predetermined liquid medicine packs. A liquid medicine from the liquid medicine injection port 71 flows into the blood storage section 32 without passing through the cardiotomy section 2, whereas a liquid medicine from the liquid medicine injection port 72 flows into the blood storage section 32 after passing through the cardiotomy section 2. The service port 73 is connected to various line tubes. The temperature probe 52 is connected to electric wiring connected to temperature measuring equipment.

Figure 3:
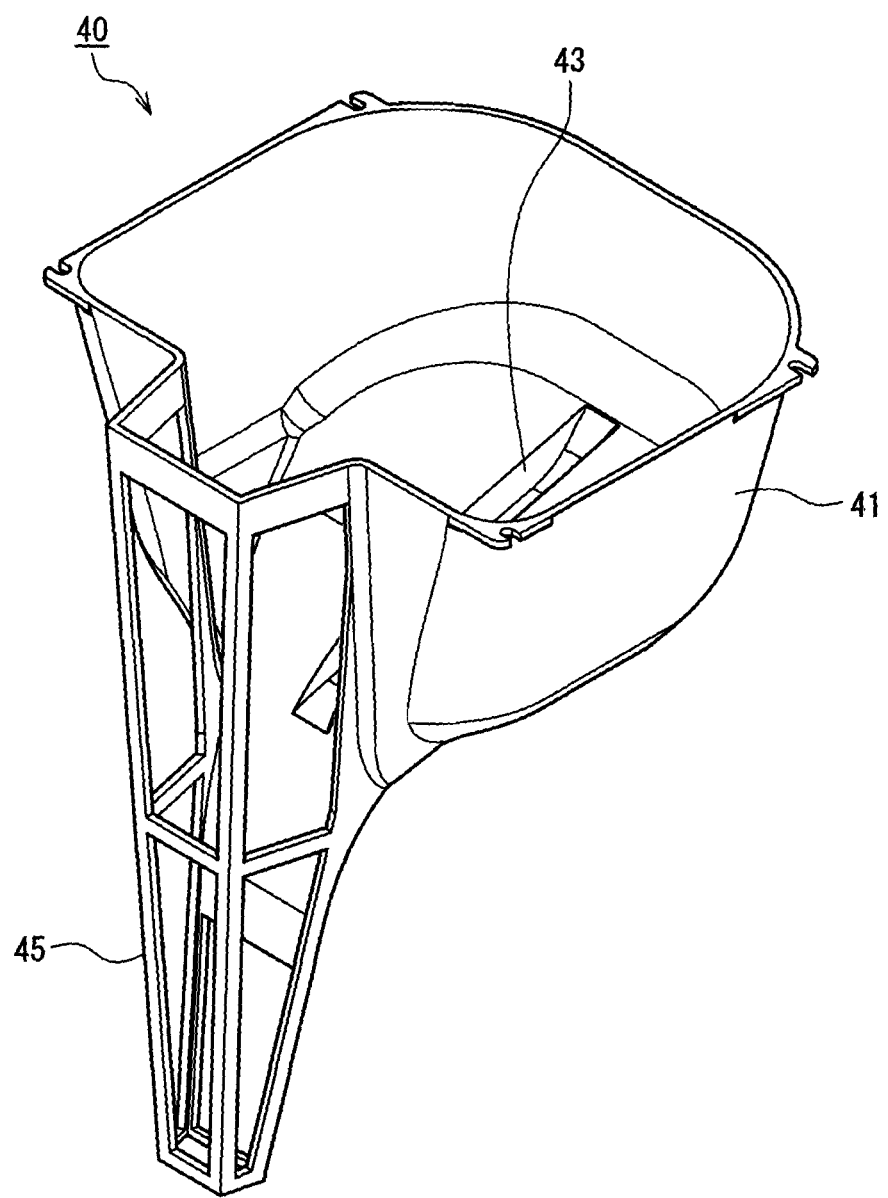
FIG. 3 is a perspective view of a support member provided in the interior of the blood reservoir illustrated in FIG. 1, according to Embodiment 1 of the present invention.

The housing 30 stores therein a support member 40 for holding a venous blood filter screen 47. FIG. 3 is a perspective view illustrating the support member 40 without holding the venous blood filter screen 47. The support member 40 includes a generally square-shaped cup section 41 and a frame section 45 composed of a lattice frame formed on one side of the cup section 41. A groove 43 is formed in the bottom of the cup section 41. The frame section 45 extends downward below the cup section 41 so that it can be inserted in the blood storage section 32 of the housing body 31. The venous blood filter screen 47 is fixed and held against the frame section 45 so as to close the openings formed on the sides of the frame section 45. The openings of the frame section 45 extend over substantially the entire vertical range of the frame section 45, with their lower ends reaching the vicinity of the blood outflow port 33.

The venous blood filter screen 47 has no particular limitations on its configuration and material as long as it has the function of a filter for removing extraneous materials or air bubbles in blood, and any known material or the like may be selected and used as appropriate. For example, a screen filter having a large number of superfine openings may be used as the venous blood filter screen 47.

The venous blood inflow port 51 and the upper end of a venous blood inlet tube 80 are connected via the lid 36. The venous blood inlet tube 80 is fitted into the groove 43 of the cup section 41 and guided inside the support member 40 from the cup section 41 to the frame section 45, with a lower end opening thereof located at a lower level than a minimum blood surface level B in the blood reservoir 5.

Below the intracardiac blood inflow port 50, the cardiotomy section 2 is arranged in the support member 40. The cardiotomy section 2 includes the filter 10 having a bag-like shape as a whole (or a shape similar to a paper coffee filter used to extract coffee), a defoamer 20 arranged inside the filter 10, and a resin plate 60 bonded to the upper ends of the filter 10 and the defoamer 20. The resin plate 60 has a through hole 61 formed in about the center thereof. A conduit tube 90 is inserted from above in the through hole 61. The conduit tube 90 communicates with the multiple intracardiac blood inflow ports 50 and the multiple liquid medicine injection ports 72 provided on the lid 36. A lower end (folded part) 11a of the filter 10 is in contact with the bottom of the cup section 41, which reduces foaming of the blood flowing out of the cardiotomy section 2.

The flow of blood in the blood reservoir 5 is described below briefly. The venous blood removed from a patient's vein passes through the venous blood inflow port 51 and the venous blood inlet tube 80 in sequence, flows out of the lower end opening of the venous blood inlet tube 80, passes through the venous blood filter screen 47, and flows out of the blood outflow port 33. Meanwhile, the intracardiac blood aspirated from a patient's operative field passes through an intracardiac blood inflow port 50, the conduit tube 90, and the cardiotomy section 2 in sequence, flows into the support member 40, passes through the venous blood filter screen 47, and flows out of the blood outflow port 33. In the course of this process, blood is stored temporarily in the blood storage section 32.

Figure 4:
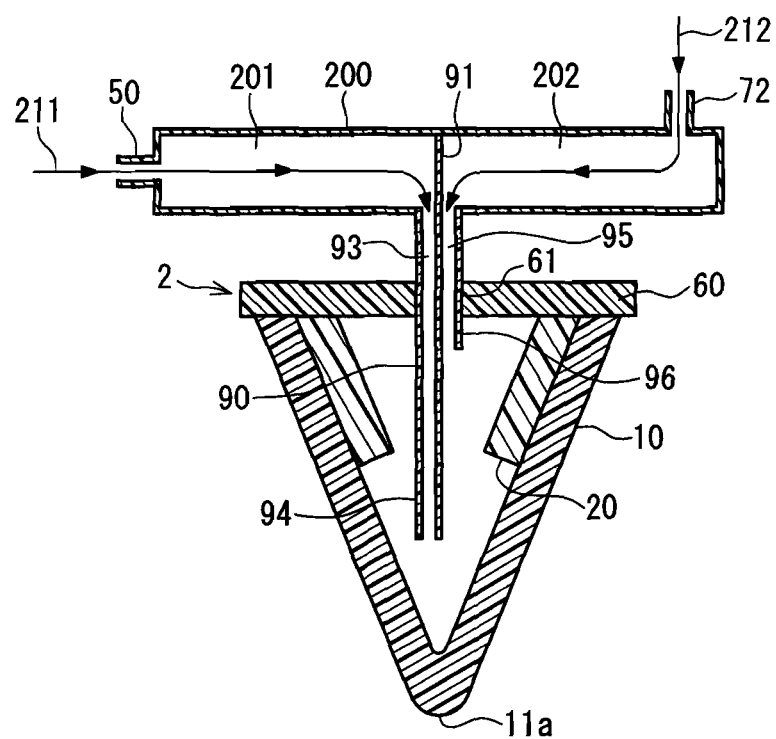
FIG. 4 is a general cross-sectional view illustrating channels of blood and a liquid medicine that flow into a cardiotomy section in the blood reservoir according to Embodiment 1 of the present invention.

FIG. 4 is a general cross-sectional view illustrating channels for the flow of blood 211 and a liquid medicine 212 from a intracardiac blood inflow port 50 and a liquid medicine injection port 72 to the cardiotomy section 2. While, in order to simplify the description, FIG. 4 illustrates the case where the conduit tube 90 communicates with only a single intracardiac blood inflow port 50 and a single chemical instillation port 72, the same applies to the case where the conduit tube 90 communicates with multiple intracardiac blood inflow ports 50 and/or multiple chemical instillation ports 72. A space in a vessel 200 provided on the lid 36 is divided by a partition wall 91 into a blood flow channel 201 for the flow of blood (intracardiac blood) and a liquid medicine flow channel 202 for the flow of a liquid medicine. The intracardiac blood inflow port 50 communicates with the blood flow channel 201, whereas the liquid medicine inflow port 72 communicates with the liquid medicine flow channel 202. A conduit tube 90 is connected to the underside of the vessel 200. The partition wall 91 also extends to the inside of the conduit tube 90. As a result, in the conduit tube 90, a blood flow channel 93 for the flow of blood (intracardiac blood) and a liquid medicine flow channel 95 for the flow of a liquid medicine are formed independently of each other on respective sides of the partition wall 91. A portion of the conduit tube 90 that forms the blood flow channel 93 is referred to as a "blood conduit tube portion 94" and a portion thereof that forms the liquid medicine flow channel 95 is referred to as a "liquid medicine conduit tube portion 96". Both of the blood conduit tube portion 94 and the liquid medicine conduit tube portion 96 have a semi-cylindrical shape, and the conduit tube 90 formed by integrating those portions has a cylindrical shape as a whole. The blood 211 flows through the intracardiac blood inflow port 50, the blood flow channel 201 in the vessel 200, and the blood flow channel 93 in the conduit tube 90 in sequence, and then into the cardiotomy section 2. The liquid medicine 212 flows through the liquid medicine injection port 72, the liquid medicine flow channel 202 in the mixing vessel 200, and the liquid medicine flow channel 95 in the conduit tube 90 in sequence, and then into the cardiotomy section 2.

In the present embodiment, since the blood flow channels 201 and 93 and the liquid medicine flow channels 202 and 95 are completely separate from and independent of each other on respective sides of the partition wall 91, the flow of blood and the flow of a liquid medicine do not affect each other. Accordingly, the problem with the conventional blood reservoir illustrated in FIG. 13, i.e., the generation of negative pressure in the liquid medicine flow channel 942 due to the aspirator effect, will not arise in the present embodiment.

Moreover, the lower end of the blood conduit tube portion 94 that forms the blood flow channel 93 is located at a lower position than the lower end of the liquid medicine conduit tube portion 96 that forms the liquid medicine flow channel 95, with respect to the vertical direction. This is because of the following reason.

As stated above, since the intracardiac blood contains many air bubbles, they float up to the blood surface in the cardiotomy section 2. Although most of such air bubbles that have floated up are broken upon coming in contact with the defoamer 20, some of them may grow and rise in the space surrounded by the defoamer 20. If the opening at the lower end of the liquid medicine conduit tube portion 96 is covered and blocked by such air bubbles, the resistance to the inflow of a liquid medicine into the cardiotomy section 2 increases. Thus, in the present embodiment, the vertical position of the lower end of the liquid medicine conduit tube portion 96 is set at such a high position so as to reduce the possibility that it comes in contact with air bubbles.

Moreover, the resistance to the inflow of a liquid medicine into the cardiotomy section 2 increases as the liquid medicine conduit tube portion 96 increases in length, irrespective of whether or not the opening at the lower end of the liquid medicine conduit tube portion 96 is blocked by air bubbles. Thus, in the present embodiment, the length of the liquid medicine conduit tube portion 96 is set as short as possible.

In view of the resistance to the inflow into the cardiotomy section 2, the blood conduit tube portion 94 is preferably as short as possible for the same reason as for the liquid medicine conduit tube portion 96. However, in the present embodiment, the blood conduit tube portion 94 is extended to a level lower than the liquid medicine conduit tube portion 96 in order to narrow the space where air bubbles can grow and rise above the blood surface by the provision of the blood conduit tube portion 94. From such a viewpoint, it is preferable that the lower end of the blood conduit tube portion 94 be located at the same position as or at a lower position than the lower end of the defoamer 20, with respect to the vertical direction.

The material for the conduit tube 90 is not particularly limited, and it may be the same material as used for the conventional conduit tube 935, such as polycarbonate. Also, the dimensions of the conduit tube 90 are not particularly limited; however, the outer diameter thereof is preferably from 8 mm to 16 mm inclusive, the inner diameter thereof is preferably from 6 mm to 12 mm inclusive, and the thickness thereof is preferably from 1.0 mm to 2.0 mm inclusive. The material for the partition wall 91 is not particularly limited, and for example, it may be the same material as used for the conduit tube 90.

Now, the cardiotomy section 2 mounted on the blood reservoir 5 according to the present embodiment will be described.

Figure 5A:
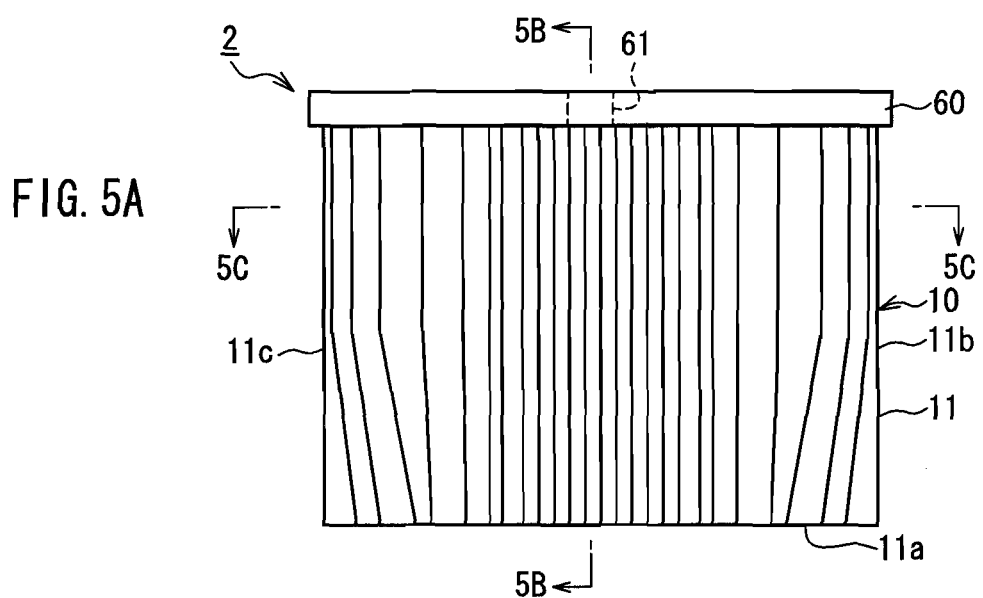
FIG. 5A is a side view of a cardiotomy section used in the blood reservoir according to Embodiment 1 of the present invention.
Figure 5B:
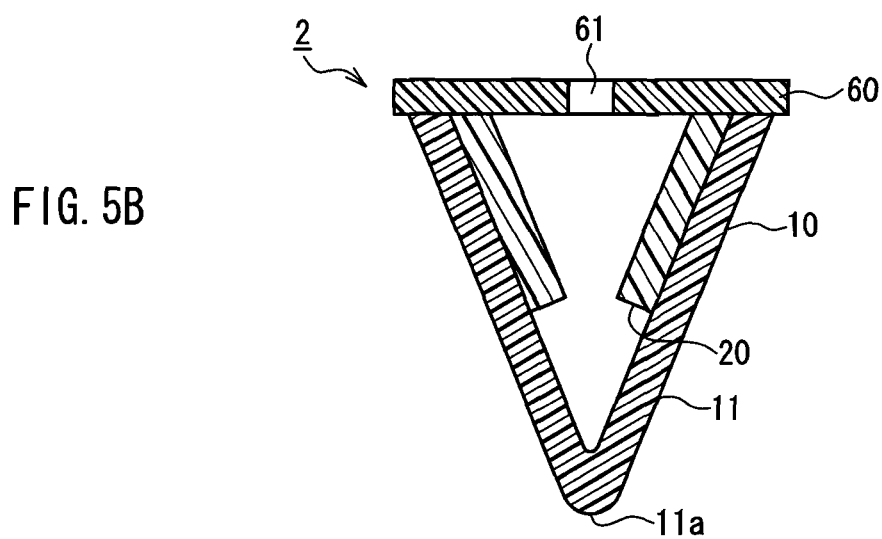
FIG. 5B is a cross-sectional view taken along the line 5B-5B in FIG. 5A.
Figure 5C:
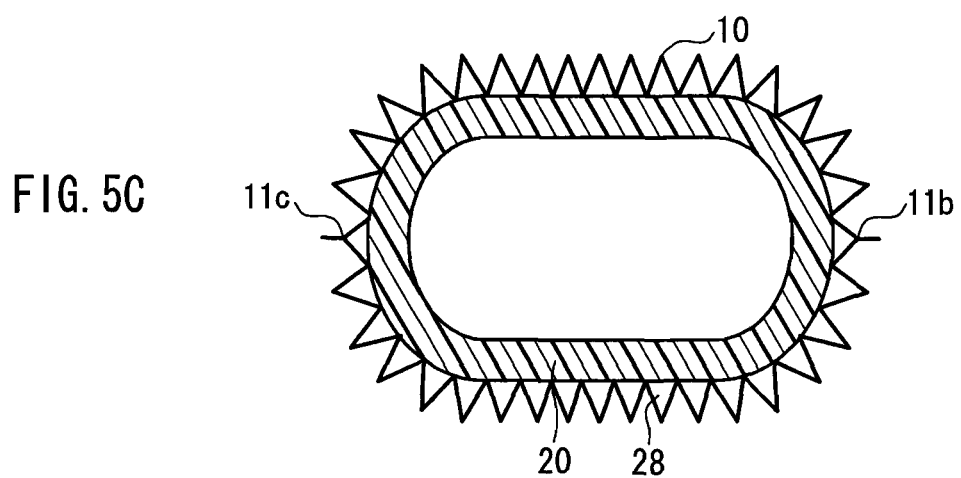
FIG. 5C is a cross-sectional view taken along the line 5C-5C in FIG. 5A.
Figure 6A:
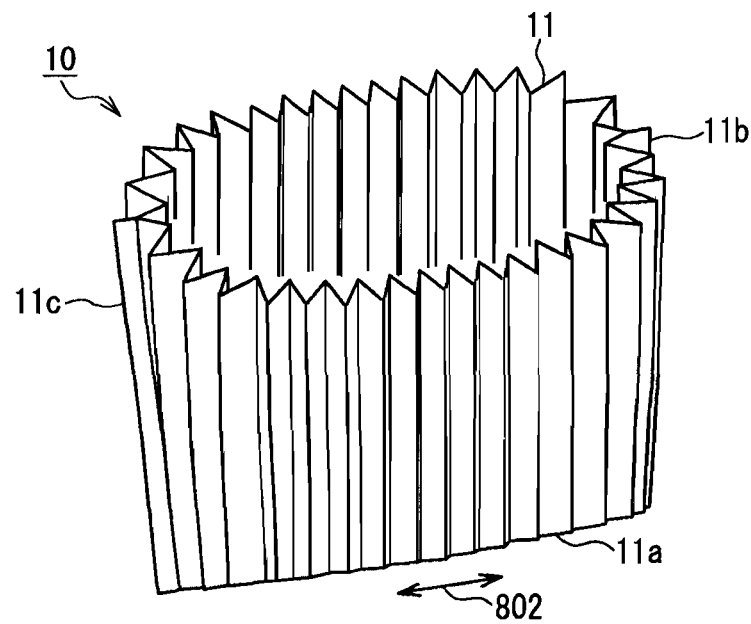
FIG. 6A is a perspective view of a filter that configures the cardiotomy section according to Embodiment 1 of the present invention.
Figure 6B:
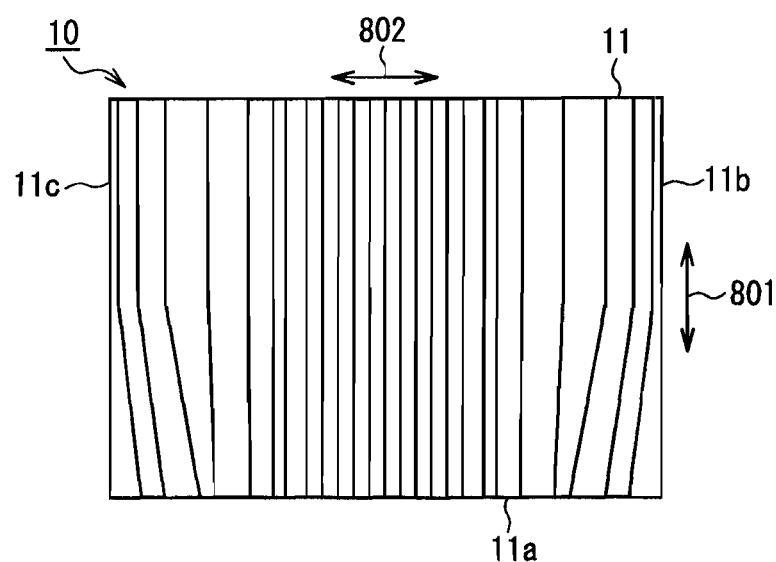
FIG. 6B is a side view of the filter illustrated in FIG. 6A.
Figure 6C:
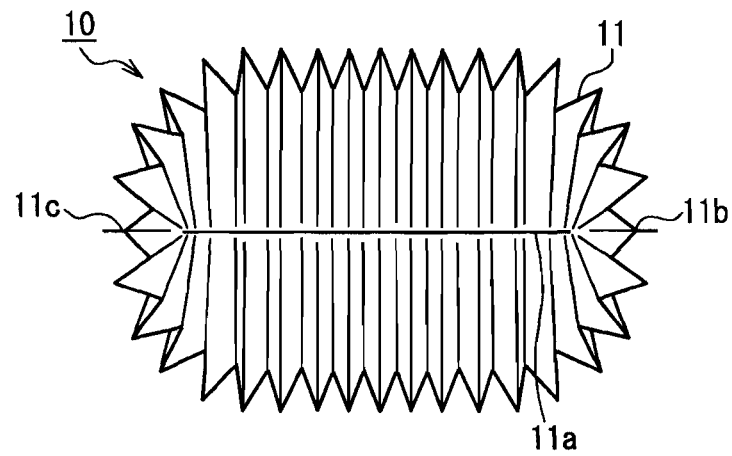
FIG. 6C is a top view of the filter illustrated in FIG. 6A.

FIG. 5A is a side view of the cardiotomy section 2, FIG. 5B is a cross-sectional view taken along the line 5B-5B in FIG. 5A, and FIG. 5C is a cross-sectional view taken along the line 5C-5C in FIG. 5A. FIG. 6A is a perspective view of the filter 10 that configures the cardiotomy section 2, FIG. 6B is a side view thereof, and FIG. 6C is a top view thereof. The filter 10 is made of a filter member 11 that is pleated along a first direction 801 in FIG. 6B. The filter member 11 has a folded part 11a that is folded along a second direction 802 intersecting with the first direction 801. The filter member 11 also is sealed at a pair of sealed edges 11b and 11c thereof that intersect with the second direction 802.

A method for manufacturing the filter 10 is described below.

Figure 7:
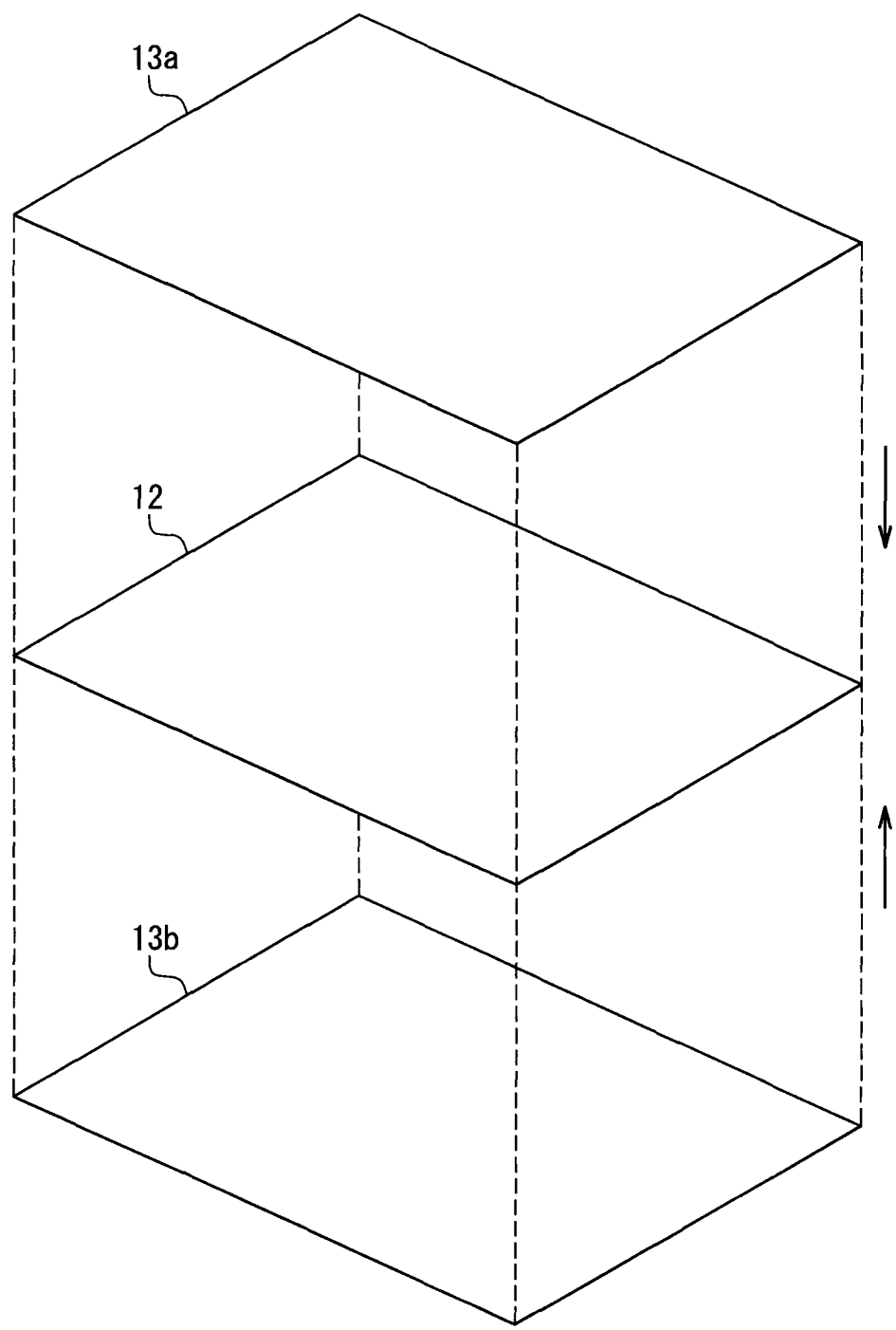
FIG. 7 is a perspective view illustrating a step for manufacturing a filter that configures the cardiotomy section according to Embodiment 1 of the present invention.

First, as illustrated in FIG. 7, support members 13a and 13b are laminated on opposite sides of a screen filter 12, which forms the rectangular filter member 11 having a three-layered laminate structure.

Figure 8:
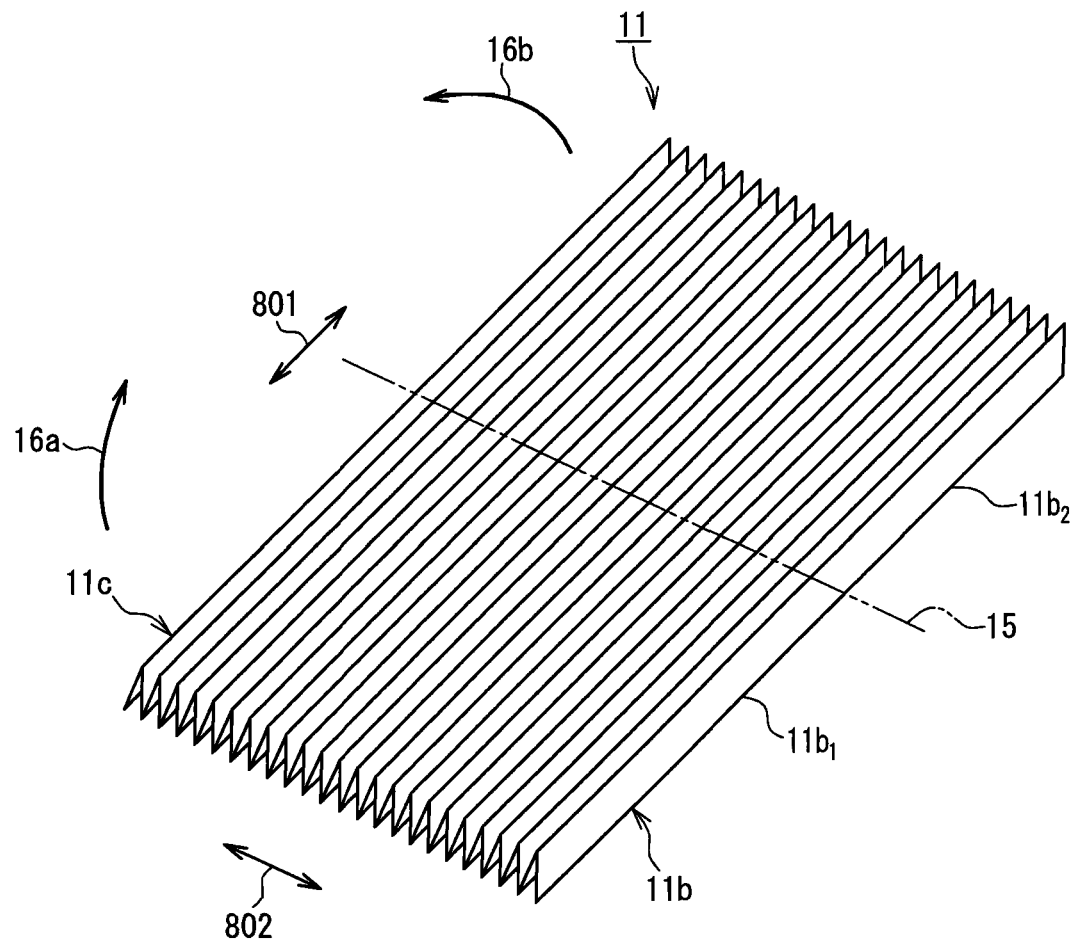
FIG. 8 is a perspective view illustrating a step for manufacturing a filter that configures the cardiotomy section according to Embodiment 1 of the present invention.

Then, as illustrated in FIG. 8, multiple pleats are formed along the first direction 801 that is parallel to one side of the rectangular filter member 11. Specifically, mountain folds and valley folds are repeated at a constant pitch along a direction parallel to the first direction 801.

The filter member 11 then is folded in the direction indicated by the arrows 16a and 16b along a fold line 15 indicated by the chain double-dashed line parallel to the second direction 802 orthogonal to the first direction 801, the fold line 15 passing through an intermediate position of the filter member 11 in the first direction 801. At this time, the filter member 11 can be folded with ease and good appearance, for example if a straight-line edge of a jig made of a hard material such as resin or metal is pressed against the filter member 11 along the fold line 15, with all the mountains (ridges) of the pleats that are in contact with the jig being displaced toward either side of the second direction 802.

Then, both edges of the filter member 11 with respect to the second direction 802 are sealed and bonded together. Specifically, referring to an edge 11b on one side with respect to the second direction 802, an edge portion $11b_1$ on one side with respect to the fold line 15 and an edge portion $11b_2$ on the other side are sealed overlapping each other. An edge 11c on the other side with respect to the second direction 802 is also sealed in a similar manner. The method of sealing is not particularly limited and may be selected as appropriate taking into consideration the material for the filter member 11 or the like, and for example, a heat seal method may be used. At this time, a material such as vinyl chloride that improves sealing properties may be inserted between the two sealed members (e.g., between the edge portions $11b_1$ and $11b_2$).

In this manner, the filter 10 having a bag-like shape as a whole (a shape similar to a paper coffee filter used to extract coffee), as illustrated in FIGS. 6A to 6C, is obtained.

The filter member 11 of the filter 10 has a three-layered laminate structure composed of the screen filter 12 and the pair of support members 13a and 13b that sandwich the screen filter 12. Because the screen filter 12 is held by being sandwiched between the pair of support members 13a and 13b having relatively high mechanical strength, the screen filter 12 can be maintained in a desired shape. In addition, since multiple pleats are formed in the filter member 11, the surface area of the filter member 11 increases, which improves the filtration efficiency and prolongs the life of the filter.

The screen filter 12 has the function of catching and removing extraneous materials in blood when the blood passes through. It further may have the function of catching air bubbles. There are no particular limitations on the screen filter 12 having such a function, and any known screen filter used in conventional cardiotomy sections may be selected and used arbitrarily. For example, a mesh filter composed of a resin material such as polyester, nylon, or polypropylene may be employed. The hole diameter of such a filter is not particularly limited, but is preferably from 20 μm to 50 μm inclusive.

The support members 13a and 13b are used to maintain the shape of the screen filter 12. They thus need to have higher mechanical strength than the screen filter 12. There are no particular limitations on the support members 13a and 13b, and any known support member used in a conventional cardiotomy section may be selected and used arbitrarily. For example, a mesh member composed of a material having good heat-sealing properties, such as polypropylene, may be employed. The hole diameter of the support members 13a and 13b preferably may be larger than the hole diameter of the screen filter 12.

The screen filter 12 and/or the support members 13a and 13b may be coated with a defoaming agent (e.g., silicone) so that they have the function of defoaming.

In FIGS. 5A to 5C, the resin plate 60 is bonded around the entire perimeter to the edge of the filter 10 on the opposite (upper) side of the filter 10 from the folded part 11a. The material for the resin plate 60 is not particularly limited; it may be an adhesive such as polyurethane, for example. In the example illustrated in FIGS. 5A and 5B, the resin plate 60 has an oval shape in plane (i.e., tracks in an athletic field). However, the shape is not limited thereto and may be selected from any arbitrary shape such as an ellipse, an circle, or a rectangle. The provision of the resin plate 60 improves the shape-keeping property of the filter 10. The resin plate 60 has formed therein the through hole 61 that allows the inflow of blood.

The defoamer 20 is, as illustrated in FIG. 5C, provided annularly along the inner peripheral face of the filter 10 inside the filter 10. The pleating of the filter 10 creates gaps 28 between the filter 10 and the defoamer 20. As illustrated in FIG. 5B, the defoamer 20 is provided in only an upper region of the filter 10 with respect to the vertical direction, and the defoamer 20 is held against the resin plate 60 by the upper edge thereof bonded to the resin plate 60. There are no particular limitations on the defoamer 20 as long as it has the function of breaking air bubbles that have come in contact, and any known defoamer used in a conventional cardiotomy section may be selected and used arbitrarily. For example, a material whose polyurethane surface as a substrate is coated with silicone oil as a defoaming agent may be employed. The form of the anti-forming material 20 may be an open-cell foam, fabric, knitted fabric, or non-woven fabric, for example. The defoamer 20 may be a single layer or may have a two or more layered laminate configuration.

Embodiment 2

Embodiment 2 according to the present invention differs from Embodiment 1 with respect to the structure at the lower end of the blood conduit tube portion 94 and in the vicinity thereof. Now, only what is different from Embodiment 1 will be described.

Figure 9:
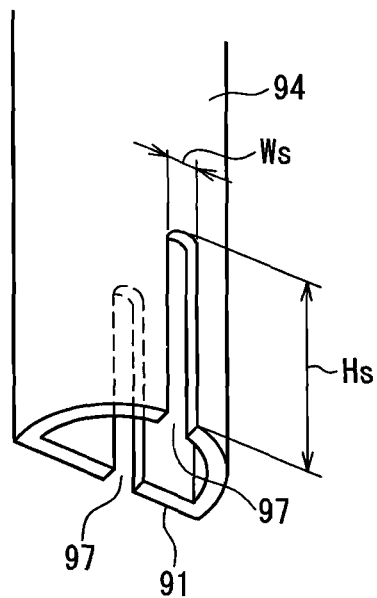
FIG. 9 is a perspective view illustrating slits formed at the lower end of a blood conduit tube portion that allows the inflow of intracardiac blood into a cardiotomy section in a blood reservoir according to Embodiment 2 of the present invention.

FIG. 9 is a perspective view of the lower end of the blood conduit tube portion 94 as viewed from below. As illustrated, a pair of slits 97 that extend upward from the lower end of the blood conduit tube portion 94 are formed in the side of the blood conduit tube portion 94. The pair of slits 97 are formed into the same shape and in the same dimensions in the cylindrical surface and the flat surface (i.e., the partition wall 91) of the semi-cylindrical blood conduit tube portion 94.

Now, the effect achieved by the pair of slits 97 will be described.

Figure 10:
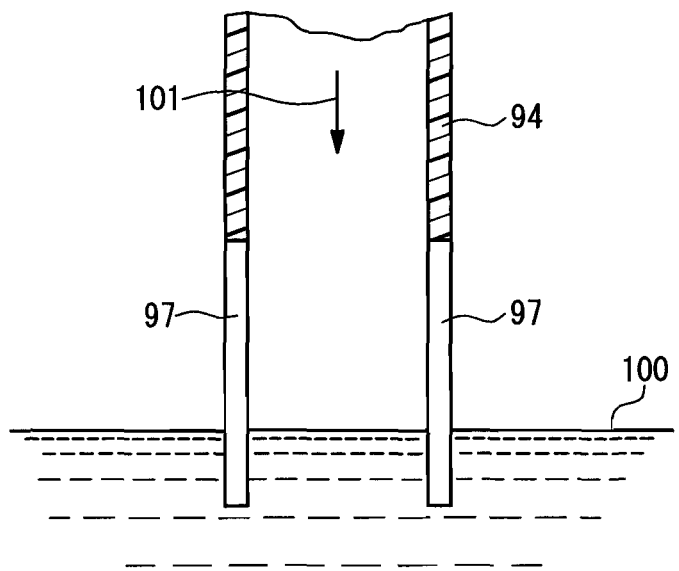
FIG. 10 is a cross-sectional view illustrating that the lower end of the blood conduit tube portion that allows the inflow of intracardiac blood into the cardiotomy section becomes immersed in blood in the blood reservoir according to Embodiment 2 of the present invention.

The lower end of the blood conduit tube portion 94 that allows the inflow of intracardiac blood into the cardiotomy section 2 generally is located at a higher level than a blood surface. However, in some cases, the blood surface level may rise for some sort of reason and thereby the lower end of the blood conduit tube portion 94 may become immersed in blood. In this case, if no slit 97 is formed in the blood conduit tube portion 94, there is a possibility that the resistance to the inflow of blood into the cardiotomy section 2 through the blood conduit tube portion 94 may increase. On the other hand, in the present embodiment, if parts of the pair of slits 97 are exposed over the blood surface even though the lower end of the blood conduit tube portion 94 becomes immersed in blood 100 as illustrated in FIG. 10, it is possible for blood (intracardiac blood) 101 flowing in through the blood conduit tube portion 94 to flow out of the blood conduit tube portion 94 through the pair of slits 97, and it is also possible to prevent an increase in atmospheric pressure in the blood conduit tube portion 94. This accordingly suppresses an increase in the resistance to the inflow of blood into the cardiotomy section 2 through the blood conduit tube portion 94. By forming the slits 97 in the blood conduit tube portion 94 in this way, it becomes possible to cope with, without problems, the case where the blood surface level rises above the lower end of the blood conduit tube portion 94.

The length $H_S$ of the slits 97 formed in the blood conduit tube portion 94 (the distance from the lower end of the blood conduit tube portion 94 to the upper end of the slits 97; see FIG. 9) is not particularly limited, but it is preferably from 5 mm to 30 mm inclusive, and more preferably from 10 mm to 20 mm inclusive. If the length $H_S$ of the slits 97 is longer than the abovementioned range, the defoaming properties may deteriorate because generated air bubbles may leak out of the blood conduit tube portion 94 from the slits 97 so that they cannot effectively be in contact with the defoamer 20. On the contrary, if the length Hs of the slits 97 is shorter than the abovementioned range, it is difficult to achieve the above-described effect with the slits 97.

Also, the width $W_S$ of the slits 97 formed in the blood conduit tube portion 94 (the circumferential dimension of the blood conduit tube portion 94; see FIG. 9) is not particularly limited, but it is preferably from 1 mm to 5 mm inclusive, and more preferably from 2 mm to 3 mm inclusive. If the width Ws of the slits 97 is wider than the abovementioned range, the defoaming properties may deteriorate for the same reason as in the abovementioned case where the length Hs of the slits 97 is too long. On the contrary, if the width Ws of the slits 97 is narrower than the above-mentioned range, it is difficult to achieve the above-described effect with the slits 97.

In the foregoing description, while the number of slits 97 formed in the blood conduit tube portion 94 is two, the present invention is not limited thereto, and the number of slits may be one or more than two. In the case where multiple slits 97 are formed, all the slits 97 do not necessarily have the same length Hs and the same width Ws and they may have different lengths and widths.

Figure 11:
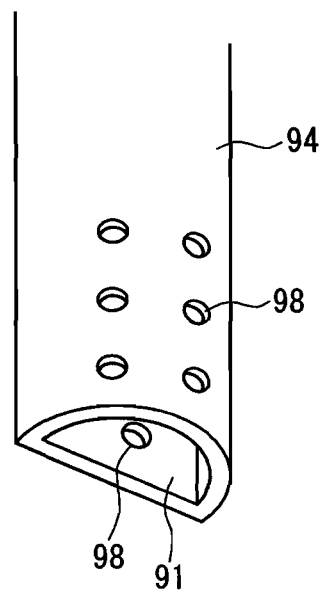
FIG. 11 is a perspective view illustrating through holes formed in the vicinity of the lower end of the blood conduit tube portion that allows the inflow of intracardiac blood into the cardiotomy section in another blood reservoir according to another embodiment of the present invention.

Instead of forming the slits 97 in the side of the blood conduit tube portion 94, through holes 98 may be formed at positions on the side of the blood conduit tube portion 94 and in the vicinity of the lower end thereof as illustrated in FIG. 11. The through holes 98 function like the slits 97, thereby achieving the same effect as achieved with the slits 97. Such through holes 98 preferably may be formed at multiple locations. The positions of the through holes 98 are not particularly limited as long as they are formed in a region in the vicinity of the lower end of the blood conduit tube portion 94, but they preferably are formed in a region on the lower end side from a location 30 mm apart from the lower end of the blood conduit tube portion 94, and more preferably a location 20 mm apart therefrom. The opening shape, opening area, number, and locations of the through holes 98 may be set as appropriate taking into consideration the volume of blood flowing through the blood conduit tube portion 94, a conceivable blood surface level, or the like. Alternatively, both the slits 97 formed as illustrated in FIG. 9 and the through holes 98 illustrated in FIG. 11 may be formed in the blood conduit tube portion 94.

The above-described Embodiments 1 and 2 are merely examples, so the present invention is not limited thereto and various modifications thereto are possible.

While the above-described Embodiments 1 and 2 employ the filter 10 in which the filter member 11 including the screen filter 12 is pleated and formed into a bag-like shape, a filter of the cardiotomy section is not limited thereto. For example, a filter in which a non-woven fabric is formed into a bag-like shape without pleating may be used.

While the lower end 11a of the above-described cardiotomy section 2 is formed in a straight line, the present invention is not limited thereto, and they may be formed in a curve, for example. The lower end 11a is preferably formed in conformity with the surface shape of a member in the blood reservoir (e.g., the bottom of the cup section 41 or the venous blood inlet tube 80) so that, when the cardiotomy section is mounted on the blood reservoir, the area of contact between the lower end 11a and the member is as large as possible. Such an increase in the area of contact between the lower end 11a and the member in the blood reservoir allows the blood from the cardiotomy section to flow over the lower end 11a and the member in contact therewith to reach the blood storage section 32, thus preventing the foaming of blood flowing out of the cardiotomy section.

In the above-described cardiotomy section 2, although the defoamer 20 is held by being bonded to the resin plate 60, the method for holding the defoamer 20 is not limited thereto. For example, the defoamer 20 may be held with a jig that is provided at the lower end of the defoamer 20 so as to prevent the defoamer 20 from moving down with respect to the filter 10.

Figure 13:
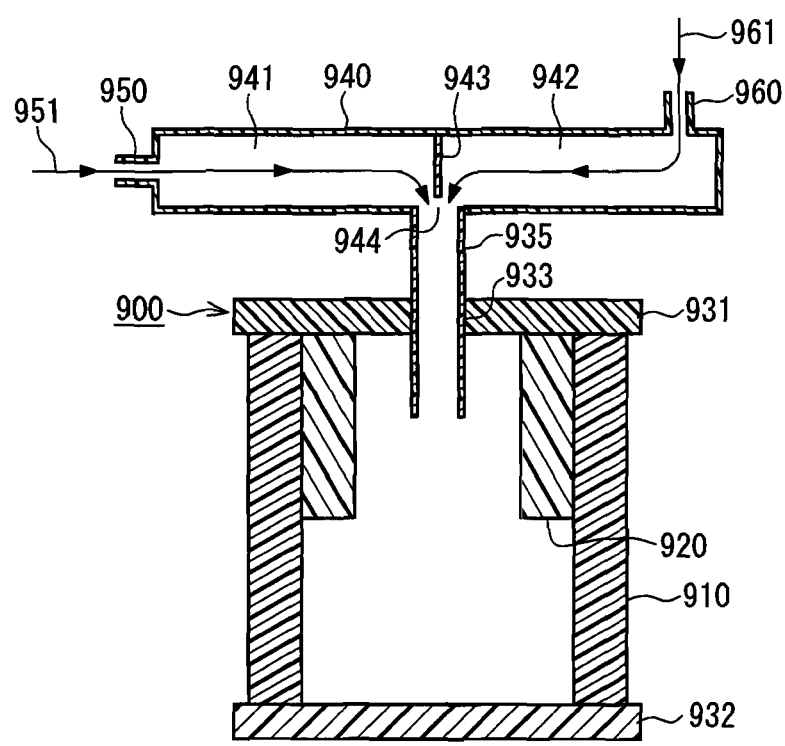
FIG. 13 is a cross-sectional view illustrating an example of a general configuration of a conventional cardiotomy section.

The cardiotomy section is not limited to the one that includes a filter formed into a bag-like shape as illustrated in FIG. 5 and it may include, for example, a filter 910 having a generally cylindrical shape as illustrated in FIG. 13. The cardiotomy section 2 in FIG. 5, however, does not include the lower resin plate 932 of the cardiotomy section 900 in FIG. 13 and thus can have excellent initial permeability and can reduce priming volume and remaining blood volume. Here, the initial permeability is determined by the volume of liquid filler that is required for the liquid filler to start to flow out of the filter 10 when the liquid filler first flows into the cardiotomy section 2 through the conduit tube 90. Excellent initial permeability reduces the blood volume, i.e., a circuit filling volume that is required to fill in the extracorporeal circulation circuit. Such reduced circuit filling volume reduces the volume of blood that is transferred from a patient's body to outside the body, thus reducing the burden on the patient. The priming volume is a total volume of a static filling volume that exists before circulation and a redundant fluid volume necessary for circulation, and it also includes the volume of fluid left in the filter 10 or the like. A low priming volume not only reduces the circuit filling volume but also improves responsiveness to fluctuations in the blood volume in the blood reservoir, thus reducing an operator workload at the time of controlling and adjusting the blood surface level. Remaining blood refers to blood that is left in the cardiotomy section 2 after the termination of extracorporeal circulation of blood. With a low remaining blood volume, the volume of blood that is returned to a patient increases, and the burden on the patient is reduced accordingly.

The blood reservoir according to the present invention is not limited to an integral type of an cardiotomy reservoir and a venous blood reservoir, such as the above-described blood reservoir 5, that allow the inflow of both venous blood and intracardiac blood, it may be any other known blood reservoir. For example, it may be an cardiotomy reservoir that does not allow the inflow of venous blood.

EXAMPLES

Example 1

Figure 12:
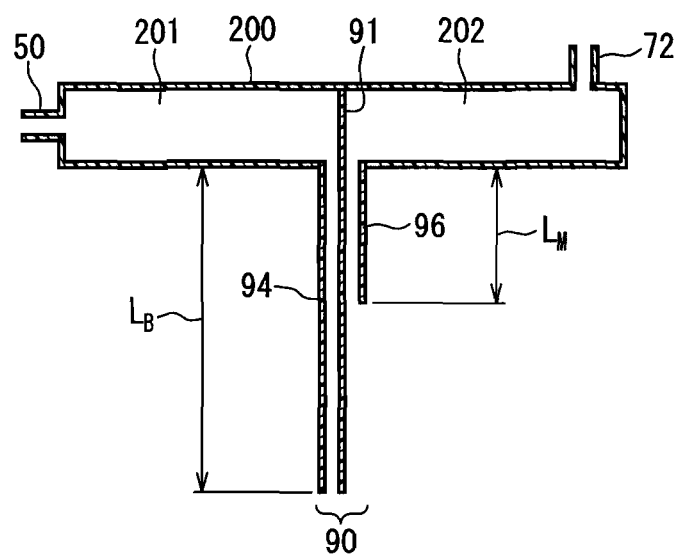
FIG. 12 is a cross-sectional view illustrating model channels from the intracardiac blood inflow port to the conduit tube and from the liquid medicine injection port to the conduit tube, used in Example 1.

Model channels from an intracardiac blood inflow port 50 to a conduit tube 90 and from a liquid medicine injection port 72 to the conduit tube 90 as illustrated in FIG. 12 were created from polycarbonate as a transparent resin. The intracardiac blood inflow port 50 was formed into a cylinder having an inner diameter of 6.0 mm, the liquid medicine injection port 72 was formed into a cylinder having an inner diameter of 4.3 mm, and a vessel 200 was formed into a hollow rectangular prism having an inner vertical dimension of 15 mm, an inner horizontal dimension of 15 mm, and an inner longitudinal dimension of 60 mm. A cylindrical conduit tube 90 having an inner diameter of 10.0 mm was connected in a central position of the bottom of the vessel 200 in the longitudinal direction. A partition wall 91 having a thickness of 1.0 mm was formed so as to divide the space in the vessel 200 and the space in the conduit tube 90 into two sections. A blood conduit tube portion 94 was formed to have a length $L_B$ of 40.0 mm, and a liquid medicine conduit tube portion 96 was formed to have a length $L_M$ of 5.0 mm.

Comparative Example 1

The same model channels as in Example 1 (see FIG. 13) were created, except in that the partition wall 91 was formed only inside the vessel 200 without being formed inside the conduit tube 90 and that the length $L_M$ of the liquid medicine conduit tube portion 96 was made the same, 40.00 mm, as the length $L_B$ of the blood conduit tube portion 94.

Evaluation

Blood that contains no air bubble (at a temperature of 25 degrees) was caused to flow through the intracardiac blood inflow port 50 and then out of the blood conduit tube portion 94 at a constant flow rate. Prior to and during the inflow of this blood, the pressure in the liquid medicine flow channel 202 in the vessel 200 was measured with a water column monometer mounted on the liquid medicine injection port 72. Then, a variation in the pressure between prior to and during the inflow of the blood (between prior pressure and in-process pressure) was obtained.

When the flow rate of blood was $1.0 \times 10^{-3}$ m³/min and $2.0 \times 10^{-3}$ m³/min, a variation in pressure in the liquid medicine flow channel 202 was 0 Pa in either case in Example 1, whereas it was −29.4 Pa and −245 Pa, respectively, in Comparative Example 1. This verified that the provision of the partition wall 91 in the conduit tube 90 as in Example 1 prevented the pressure in the liquid medicine flow channel 202 from being lowered due to the inflow of blood into the cardiotomy section.

The above-described embodiments and examples merely are intended to clarify the technical contents of the present invention and the present invention should not be interpreted to be limited to those embodiments and examples. Various modifications are possible within the scope of the claims and the spirit of the present invention, and the present invention should be interpreted broadly.

INDUSTRIAL APPLICABILITY

The present invention is widely applicable to blood reservoirs that are provided in an extracorporeal circulation circuit used in cardiopulmonary surgeries or the like.

The invention claimed is:

1. A blood reservoir comprising:
a housing including an intracardiac blood inflow port configured to receive intracardiac blood aspirated from a patient's operative field, a liquid medicine injection port in an upper portion of the housing configured to receive a liquid medicine, and a blood outflow port at a lower end of the housing;
a cardiotomy section arranged in the housing, the cardiotomy section including a filter that filters the intracardiac blood; and
a conduit tube that communicates with the intracardiac blood inflow port and the liquid medicine injection port and allows the intracardiac blood from the intracardiac blood inflow port and the liquid medicine from the liquid medicine injection port to flow into the cardiotomy section,
the conduit tube being inserted from above downward in the cardiotomy section,
wherein a blood flow channel for flow of the intracardiac blood and a liquid medicine flow channel for flow of the liquid medicine are formed in separate flow passages in the conduit tube,
a lower end of a blood conduit tube portion that forms the blood flow channel is located at a lower position than a lower end of a liquid medicine conduit tube portion that forms the liquid medicine flow channel, with respect to a vertical direction, and
the lower end of the blood conduit tube portion and the lower end of the liquid medicine conduit tube portion are disposed in the cardiotomy section such that the intracardiac blood and the liquid medicine are mixed in the cardiotomy section after exiting from the blood conduit tube portion and the liquid medicine conduit tube portion, respectively, and before traveling through the filter.

2. The blood reservoir according to claim 1, wherein a slit that extends upward from the lower end of the blood conduit tube portion is formed in a side of the blood conduit tube portion, or a through hole is formed at a position in a side of the blood conduit tube portion and in the vicinity of the lower end thereof.

3. The blood reservoir according to claim 2, wherein a length $H_S$ from the lower end of the blood conduit tube portion to an upper end of the slit is from 5 mm to 30 mm inclusive.

4. The blood reservoir according to claim 2, wherein the slit has a width $W_S$ of 1 mm to 5 mm inclusive.

5. The blood reservoir according to claim 1, wherein the blood flow channel for flow of the intracardiac blood and the liquid medicine flow channel for flow of the liquid medicine are formed in the same conduit tube and share a common side wall.

6. The blood reservoir according to claim 1, wherein the liquid medicine injection port is configured to receive a liquid medicine that does not include blood.

7. The blood reservoir according to claim 1, wherein the intracardiac blood inflow port and the liquid medicine injection port are positioned separate from each other.

* * * * *

UNITED STATES PATENT AND TRADEMARK OFFICE
CERTIFICATE OF CORRECTION

PATENT NO. : 8,414,515 B2
APPLICATION NO. : 12/675053
DATED : April 9, 2013
INVENTOR(S) : Katsuno et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 192 days.

Signed and Sealed this
Nineteenth Day of November, 2013

Teresa Stanek Rea
*Deputy Director of the United States Patent and Trademark Office*